United States Patent [19]

Johnson et al.

[11] 4,452,986
[45] Jun. 5, 1984

[54] IMIDAZOLYL-SUBSTITUTED BENZOFURANS

[75] Inventors: Roy A. Johnson, Norfolk County, Mass.; Chiu-Hong Lin; Gordon L. Bundy, both of Kalamazoo County, Mich.

[73] Assignee: The Upjohn Company, Kalamazoo, Mich.

[21] Appl. No.: 430,295

[22] Filed: Sep. 30, 1982

Related U.S. Application Data

[63] Continuation-in-part of Ser. No. 385,620, Jun. 8, 1982, abandoned.

[51] Int. Cl.³ .......................................... C07D 405/06
[52] U.S. Cl. .............................. 548/336; 424/273 R; 544/139; 544/370; 546/196
[58] Field of Search ........................................ 548/336

[56] References Cited

U.S. PATENT DOCUMENTS 4,112,224  9/1978  Bundy ............................... 542/426
4,259,338  3/1981  Paioni et al. ........................ 424/267
4,410,539  10/1983 Cross et al. ..................... 424/273 R

FOREIGN PATENT DOCUMENTS 50957      5/1982  European Pat. Off. .
2537837    3/1976  Fed. Rep. of Germany .
2039903A   8/1980  United Kingdom .

OTHER PUBLICATIONS

D. Harris et al., *Advances in Prostaglandin and Thromboxane Research* 6:437 (1980).
T. Miyamoto et al., *Advances in Prostaglandin and Thromboxane Research* 6:443 (1980).
H. Tai et al., *Advances in Prostaglandin and Thromboxane Research* 6:447 (1980).

*Primary Examiner*—Richard A. Schwartz
*Attorney, Agent, or Firm*—Lawrence T. Welch

[57] ABSTRACT

The present invention provides novel imidazolyl-benzofurans and derivatives thereof which are useful as thromboxane $A_2$ ($TXA_2$) synthetase inhibitors and as such represent potent pharmacological agents.

7 Claims, No Drawings

IMIDAZOLYL-SUBSTITUTED BENZOFURANS

DESCRIPTION

Cross Reference To Related Applications

This application is a continuation in part of application Ser. No. 385,620, filed June 8, 1982, now abandoned.

BACKGROUND OF THE INVENTION

The present invention relates to novel compositions of matter. More particularly, the present invention relates to imidazolyl-substituted benzofurans and and derivatives thereof. These compounds are potent thromboxane $A_2$ inhibitors and as such represent useful pharmacological agents.

Since the discovery that human platelets convert the prostaglandin endoperoxide ($PGH_2$) into a labile proaggregatory molecule known as thromboxane $A_2$ ($TXA_2$), researchers have sought compounds that could selectively inhibit the biological activity of $TXA_2$. This end may be achieved in two different ways: the synthesis of $TXA_2$ can be blocked by inhibiting the $TXA_2$ synthetase, or a compound could be a receptor level antagonist of $TXA_2$. As therapeutic agents, $TXA_2$ synthetase inhibitors are more useful. See, e.g., R. Gorman, "Biological and Pharmacological Evaluation of Thomboxane Synthetase Inhibitors," Advances in Prostaglandin and Thromboxane Research, 6:417 (1980), and references cited therein. Most important are compounds which selectively inhibit $TXA_2$ synthetase. Id.

PRIOR ART

A number of $TXA_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)-1H-imidazole] disclosed in D. Harris, et al., Advances in Prostaglandin and Thromboxane Research 6:437 (1980); pyridine and its derivatives, disclosed in T. Miyamoto, et al., Advances in Prostaglandin and Thromoboxane Research, 6:443 (1980), and British patent application No. 2,039,903A (abstracted in Derwent Farmdoc No. 50111C (1980)). See also H. Tai, et al., Advances in Prostaglandin and Thromboxane Research, 6:447 (1980). Other compounds which have been disclosed as thromboxane synthetase inhibitors, include sodium p-benzyl-4(1-oxo-2-(4-chlorobenzyl)-3-phenylpropyl)-phenyl phosphate, imidazoles, nordihydroguaiaretic acid, and 12L-hydroperoxy-5,8,10,14-eicosatetraenoic acid (HETE). As noted in the above named British patent specification, however, the inhibitory activity of these latter compounds on thromboxane synthetase is very weak making them unsatisfactory as practically effective medicines.

Tetrahydropyridinyl- and piperidinyl-substituted benzofurans are disclosed in U.S. Pat. No. 4,259,338 as psychopharmaceuticals and antidepressants. Similar compounds are disclosed in German Offenleggunschrift No. 2,537,837.

SUMMARY OF THE INVENTION

Thus, the present invention particularly provides:
A compound of the formula I wherein $Z_3$ is
(a) imidazolyl, or
(b) imidazolyl substituted by $(C_1-C_3)$alkyl; wherein $X_3$ is (a) $-(CH_2)_n-$,
(b) $-C(OH)-$, or
(c) $-C(O)-$;

wherein $R_1$ is hydrogen, a pharmacologically acceptable cation, $(C_1-C_{12})$ alkyl, $(C_3-C_{10})$ cycloalkyl, $(C_7-C_{12})$ aralkyl, phenyl, phenyl mono-, di-, or trisubstituted by chloro, $(C_1-C_3)$ or alkyl, or phenyl para-substituted by
(a) $-NHCO-R_{25}$,
(b) $-O-CO-R_{26}$,
(c) $-CO-R_{24}$,
(d) $-O-CO-(p-Ph)-R_{27}$, or
(e) $-CH=N-NH-CO-NH_2$, wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy; and $R_{27}$ is hydrogen or acetamido, and wherein $-(p-Ph)-$ is 1,4-phenylene;

wherein $R_4$ is
(a) hydrogen,
(b) $(C_1-C_4)$alkyl, or
(c) phenyl;

wherein $R_7$ is
(a) hydrogen,
(b) $-CH_2OH$,
(c) $-COOR_1$,
(d) $-CH_2N(R_4)_2$,
(e) $-CN$
(f) $-CON(R_4)_2$, or
(g) $-C(O)-R_4$;

wherein $R_9$ and $R_{12}$ are the same or different and are
(a) hydrogen,
(b) $(C_1-C_4)$alkyl
(c) fluoro,
(d) chloro,
(e) bromo,
(f) $-OCH_3$, or,
(g) when taken together and attached to contiguous carbon atoms, $-O-CH_2-O-$;

wherein D represents a single or a double bond; and wherein m and n are the same or different and are the integers 0 to 4, inclusive; including, pharmacologically acceptable acid addition salts thereof; and when D represents a single bond, an enantiomer or a racemic mixture of enantiomers thereof.

The carbon atom content of various hydrocarbon-containing moieties is indicated by a prefix designating the minimum and maximum number of carbon atoms in the moiety, i.e., the prefix $(C_i-C_j)$ indicates a moiety of the integer "i" to the integer "j" carbon atoms, inclusive. Thus $(C_1-C_3)$alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 3 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
1-methylpiperidine,
4-ethylmorpholine,
1-isopropylpyrrolidine,
2-methylpyrrolidine,
1,4-dimethylpiperazine,
2-methylpiperidine,
and the like, as well as amines containing water-solubilizing or hydrophilic groups, e.g.,
mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
glactamine,
N-methylglycamine,
N-methylglucosamine,
ephedrine,
phenylephrine,
epinephrine,
procaine,
and the like. Further useful amine salts are the basic amino acid salts, e.g.,
lysine and
arginine.

Examples of suitable pharmacologically acceptable quaternary ammonium cations are
tetramethylammonium,
tetraethylammonium,
benzyltrimethylammonium,
phenyltriethylammonium, and the like.

Pharmaceutically acceptable acid addition salts are formed at the heterocyclic amine moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art.

The compounds of the present invention will be named herein as benzofurans, using the Chemical Abstracts numbering system (see Naming and Indexing of Chemical Substances for Chemical Abstracts during the Ninth Collective Period (1972–1976), a reprint of section IV from the Volume 76 Index Guide.)

The compounds of the present invention were tested for $TXA_2$ inhibition as follows:

Rabbit aortic strips were superfused in series with Krebs solution. Thromboxane $A_2$ ($TXA_2$) was generated by mixing prostaglandin $H_2$ ($PGH_2$) with human platelet microsomes (HPM).

Potential inhibitors were tested by comparing the response of the rabbit aorta to the amount of $TXA_2$ produced by mixing $PGH_2$ and HPM without the test compound in the reaction medium and then the amount of $TXA_2$ produced when the test compound was added to the HPM 5 minutes before the HPM was mixed with $PGH_2$. By this means compounds which selectively inhibit $TXA_2$ synthetase are found. For a discussion of $TXA_2$ synthetase inhibition testing see, e.g., R. Gorman, supra.

Using this test system, one compound, 5-N-imidazolylmethylbenzofuran-2-carboxylic acid, sodium salt (Example 3), has been shown to be the most effective in inhibiting $TXA_2$ formation. This compound has an approximate $ED_{50}$ in this system of between 10 and 100 ng/ml.

The novel compounds of this invention have thus been shown to be highly active as selective inhibitors of the thromboxane synthetase enzyme system. Accordingly, these novel compounds are useful for administration to mammals, including humans, whenever it is desirable medically to inhibit this enzyme system. For a discussion of the utility of $TXA_2$ inhibitors, see, e.g., Derwent Farmdoc Nos. 18399B; 72896B; 72897B; 63409B; 03755C; 03768C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg to about 500 µg/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Thromboxane synthetase converts $PGH_2$ (prostaglandin endoperoxide) into $TXA_2$. $PGH_2$ is also converted to prostacyclin, $PGD_2$, and other compounds by other enzymes. Thus, because the compounds of this invention inhibit thromboxane $A_2$ synthetase, they increase the $PGH_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the American Society for Cell Biology, in the Journal of Cell Biology, 87:64 (1980).

Similarly, prostacyclin has been shown to be an effective antihypertensive agent. The compounds of the present invention are also used for this purpose. (See, e.g., British patent specification No. 2,039,903A).

For a general discussion of the utility of $TXA_2$ synthetase inhibitors which increase endogenous prostacyclin, see, Aiken, et al. J. Pharmacol. Exp. Ther., 219:299 (1981).

The compounds of the present invention are prepared by the methods depicted in Chart A-I.

Thus, the compounds of the present invention wherein m is zero are prepared by the method of Chart A. In Chart A, $R_{10}$ is all substituents within the scope of $R_1$ excluding the pharmacologically acceptable cations. All other variables in Chart A are defined as above. A hydroxybenzaldehyde of the Formula X is cyclized into the compounds of the present invention by methods known in the art. See, e.g., S. Tanaka, J. Am. Chem. Soc., 73:872 (1951). Thus, the compound may be reacted with diethyl bromomalonate in the presence of potassium carbonate to yield the desired benzofuran-2-carboxylic acid ester. See, e.g., D. T. Witiak, et al., J. Med. Chem. 21:833 (1978). Higher yields are obtained when the reaction conditions are changed so that the compound is reacted in the presence of sodium hydride in toluene (solubilized with dicyclohexyl-18-crown-6). The ethyl-benzofuran-2-carboxylate of the formula XV is alkyl chlorinated by treatment with paraformaldehyde and zinc chloride to yield the formula XVI compound. The Formula XVI compound thus formed is reacted with imidazole or an alkyl substituted imidazole to yield the formula XVII product.

Conversion of the ester of the Formula XVII to the desired pharmacologically acceptable salts or the free acid is accomplished by known methods.

Compounds of the present invention when $X_1$ is $-(CH_2)_n-$ and n is 2, 3, or 4 are prepared according to Chart B. A hydroxybenzaldehyde of the Formula LXXI (wherein P is 0, 1, or 2) is reacted with an appropriate pyridinylalkyltriphenylphosphonium chloride of the Formula LXXII in the presence of n-butyllithium to yield the unsaturated hydroxyphenylalkylpyridine of the Formula LXXIII. Catalytic reduction of the olefinic bonds yields the alkylene bridged compounds of the formula LXXIV.

For compounds wherein m is one, the method of Chart C is used. An ester of the Formula XL is reduced with lithium aluminum hydride in ether or tetrahydrofuran to yield the corresponding alcohol after workup. This alcohol is tosylated or mesylated using p-toluenesulfonyl chloride or methanesulfonyl chloride in pyridine to yield the Formula XLII product. (Ts indicates the tosylated compound, but the compound could also be mesylated). This compound is treated with excess sodium cyanide in dimethylformamide (DMF) and stirred under nitrogen at room temperature for 5 hr to yield the Formula XLIII cyano compound. This compound is dissolved in ethanol and treated with 25% aqueous potassium hydroxide to yield the corresponding acid. This compound is esterified by means well known in the art, e.g., treatment with diazomethane in methanol for the methyl ester. Pharmacologically acceptable salts are also prepared by means well known in the art.

Chart D depicts the synthesis of compounds of the present invention wherein m is 2, 3, or 4. In Chart D, q is zero, one, or 2. An ester of the Formula L is reduced with diisobutylaluminum hydride (DIBAL) in toluene or methylene chloride at low temperature to yield, after workup, the Formula LI aldehyde. Reaction of this aldehyde with an alkoxy alkylene-triphenylphosphorane of the formula $Ph_3P=CHCH_2-(CH_2)_qCOOR_{10}$ (wherein Ph is phenyl) yields the unsaturated ester of the Formula LII after workup. Careful reduction of this unsaturated ester by reaction with one equivalent of hydrogen over palladium-on-carbon in alcohol yields the saturated ester of the Formula LIII. The free acid or a pharmaceutically acceptable salt of this ester is prepared by means well known in the art. The corresponding amides, phenacyl esters, and the like are prepared by the methods depicted in e.g., U.S. Pat. Nos. 4,292,445 and 4,172,206.

The dihydrobenzofurans are prepared as depicted in Chart E. A solution of a formula LX benzofuran in water is stirred with excess sodium amalgam (NaHg) for 24 hr. After workup there is obtained the corresponding Formula LXI dihydrobenzofuran. (See, e.g., D. T. Witiak, et al., J. Med. Chem. 14, 754 (1971).)

Reduction of the corresponding acid or ester of the formula $COOR_{10}$ with lithium aluminum hydride as depicted in Chart C, (XL to XLI) is used to prepare all of the corresponding alcohols within the scope of Formula I. Conversion of the alcohol to a corresponding acid addition salt is accomplished by known means.

The compounds of this invention wherein m is zero and $R_7$ is hydrogen are prepared by the method of Chart F. A formula LXXV aldehyde is reacted with an appropriate Wittig reagent (prepared by reacting sodium hydride and dimethylsulfoxide with an alkoxyalkyltriphenyl phosphonium halide) to yield the formula LXXVI enol ether. This compound is treated with perchloric acid to yield the formula LXXVII benzofuran.

Chart G depicts a method for preparing compounds wherein $X_1$ is —C(O)—. A compound of the formula CXX is treated with potassium superoxide to yield the formula CXXI compound.

Substituted benzofurans (i.e. compounds wherein $R_9$ and $R_{12}$ are other than hydrogen) are prepared by the methods depicted in Charts H and I.

Chart H depicts a method for preparing brominated derivatives. An aldehyde of the formula CX is treated with bromine to yield the corresponding brominated compound of the formula CXI, which is then converted to the compounds of the present invention by the method of Chart A.

Chart I depicts a method for preparing methyl or methoxy substituted benzofurans or benzothiophenes. In Chart I, $R_{19}$ is methyl or methoxy. The formula CXV ether is hydrolyzed (using hydrobromic acid for example) to yield the formula CXVI alcohol. Similarly, the formula CXV' ether is hydrogenolyzed with hydrogen over palladium on carbon catalyst to yield the formula CXVI alcohol. This alcohol is treated with trifluoroacetic acid in the presence of hexamethylenetetramine to yield the formula CXVII aldehyde, which is converted to the compounds of this invention by the method of Chart A.

Similarly, various substituted hydroxy benzaldehydes are available commercially or may be prepared by methods known in the art. The hydroxybenzaldehydes are thus converted to the claimed benzofurans by the method of Chart A.

Preparation of various other benzofuran derivatives within the scope of this invention are prepared by analogous procedures well known in the art.

Certain compounds of the present invention are preferred. Thus, compounds of the formula I, wherein D denotes a double bond, $X_1$ is $-(CH_2)_n-$ (wherein n is zero or one, more preferably one), $Z_1$ is imidazolyl, m is zero, $R_7$ is $COOR_1$, and $R_1$ is Na or H are preferred. Compounds having all these preferences are more preferred. Thus, 5-N-imidazolylmethyl-benzofuran-2-carboxylic acid, sodium salt (Example 3) is a preferred compound of this invention.

DESCRIPTION OF THE PREFERRED EMBODIMENTS

The present invention is seen more fully by the Examples given below.

PREPARATION 1

Ethyl Benzofuran-2-carboxylate
Refer to Chark A (conversion of X to XV).

A 3-neck round bottomed flask equipped with a mechanical stirrer, a dropping funnel, a gas inlet tube, and a thermometer is charged with 24.4 g (0.2 mol) of salicyl aldehyde (Aldrich) and 800 ml of THF-EtOH (19:1) under a nitrogen atmosphere. To this solution 150 ml (0.24 mol) of potassium t-butoxide in THF (1.6 M) is added dropwise over 20 min at room temperature. A milky yellow precipitate is formed during the addition. The mixture is stirred at room temperature for one hr. A solution of 57.4 g (0.24 mol) of diethyl bromomalonate (Aldrich) in 20 ml of THF is added dropwise over 10 min. The mixture becomes grayish in color. After stirring for one hr at room temperature, another portion of potassium t-butoxide in THF (150 ml, 0.24 mol) is added dropwise over 40 min at room temperature. TLC shows no starting material remaining after an additional 40 min of stirring. The mixture is poured into 500 ml of brine mixed with crushed ice and extracted twice with ethyl acetate (1 L). The organic phase is washed with brine and dried over anhydrous magnesium sulfate. Filtration and concentration affords a deep brown oil. Vacuum distillation affords pure ethyl benzofuran-2-carboxylate (boiling point 88°–91° C./0.03 mm, 32.5 g, 85%.)

The NMR (CDCl$_3$; TMS, δ) spectrum reveals peaks at 7.85–7.22, 4.42, and 1.40.

The IR spectrum (film, νmax) reveals peaks at 1720, 1575, 1560, 1480, 1180, 1140, 1090, 1010, 950, 890, 840, and 750 cm$^{-1}$.

The mass spectrum reveals an ion at m/e 190.0622.

The C:H ratio is 69.24:5.32.

PREPARATION 2

Ethyl 5-chloromethylbenzofuran-2-carboxylate and
Ethyl 4-chloromethylbenzofuran-2-carboxylate
Refer to Chart A (conversion of XV to XVI).

A 250 ml 3-neck (24/40) round bottomed flask, equipped with a magnetic stirring bar, a condenser and a gas bubbler, is charged with a solution of 32.13 g (0.169 mol) of ethyl benzofuran-2-carboxylate (Preparation 1) dissolved in 85 ml of chloroform. Paraformaldehyde (6.7 g, 0.22 mol) and zinc chloride (6.1 g, 0.045 mol) (dried at 100° C. under vacuum for 2 days) are added. The resulting mixture is heated to 50° C. and anhydrous hydrogen chloride gas is bubbled slowly through the magnetically stirred mixture. The mixture gradually turns black in color and after stirring for 4 hr TLC analysis indicates only about a 50% conversion to the titled products. Another 6.7 g of paraformaldehyde (0.22 mol) is added and the resulting mixture is stirred for an additional hr. Little change in the course of the reaction is observed by TLC. The mixture is cooled, diluted with chloroform and washed consecutively with water, saturated aqueous sodium bicarbonate and brine. Drying (MgSO$_4$), filtration and concentration afford 40.98 g of crude product mixture as a dark brown oil.

This mixture is chromatographed on a column containing 1.5 kg of silica gel 60 eluting with Skellysolve B-ethyl acetate (19:1) fractions 7–13 afford unreacted starting material (10.6 g, 33%) (fractions 1–9, 1000 ml; fractions 10–13, 400 ml). Fractions 15–29 (400 ml) contained a mixture of the desired products ethyl 5- (and 4-)chloromethyl-benzofuran-2-carbonylate (18.2 g, 45%) and fractions 30–47 (400 ml) afford 2.1 g (4.3%) of ethyl 4,5-bischloromethylbenzofuran-2-carboxylate.

The NMR (CDCl$_3$; TMS, $\delta$) spectrum reveals peaks at 7.82–7.10, 4,82, 4.45, and 1.40.

The IR (film, $\nu$max) spectrum peaks are observed at 2970, 1720, 1570, 1470, 1440, 1370, 1320, 1300, 1230, 1190, 1140, 1005, 945, 770, 750, 700, and 620 cm$^{-1}$.

The mass spectrum reveals ions at m/e 238.0384, 204, 193, 175, 159, 131, and 102. (The methyl ester of this compound is also disclosed in U.S. Pat. No. 2,754,286.)

EXAMPLE 1

Ethyl 5-N-imidazolylmethyl-benzofuran-2-carboxylate and Ethyl 4-N-Imidazolylmethyl-benzofuran-2-carboxylate (Formula I: Z$_3$ is imidazolyl, X$_3$ is —CH$_2$— and is para or meta to the oxygen, R$_9$, R$_{12}$, and R$_2$ are hydrogen, D is a double bond, m is zero, and R$_7$ is —COOCH$_2$CH$_3$)

Refer to Chart A (conversion of XVI to XVII).

A two-neck round-bottomed flask equipped with a magnetic stirring bar is charged with 0.264 g (5.5 mmol) of sodium hydride (50% active) under a nitrogen atmosphere. The hydride is washed twice with dry hexane and suspended in 10 ml of DMF. Imidazole (0.375 g, 5.5 mmol) dissolved in 2 ml of DMF is added dropwise over a period of 5 min. Gas evolution started immediately. The mixture is warmed to 90° C. with stirring for one hr. The resulting clear, yellow solution is then cooled to room temperature and a solution of 1.2 g (5.0 mmol) of ethyl 5- (and 4-)chloro-benzyofuran-2-carboxylate in DMF is added dropwise over a period of 5 min. A white precipitate starts to appear. The mixture is stirred at room temperature for 40 min and quenched with brine. Extraction with ethyl acetate is followed by washing the organic layer with water and brine. After drying the solution over anhydrous magnesium sulfate, the solution is filtered and concentrated in vacuo. Liquid chromatography (LC) is carried out by using 324 g silica gel 60 (40–63 $\mu$g), eluting with methylene chloride-acetone-ethanol (5:10:0.1) and collecting 40 ml fractions. Fractions homogeneous on TLC are combined and concentrated in vacuo to give the following products: Fractions 27–30 give a pure ethyl 4-N-imidazolylmethyl-benzofuran-2-carboxylate as an oil, (0.272 g, 20%) and fractions 32–42 give pure ethyl 5-N-imidazolylmethyl-benzofuran-2-carboxylate (0.825 g, 61%) (crystallized from ethyl acetate-hexane, with melting point of 96°–98° C.).

The NMR (CDCl$_3$; TMS, $\delta$) spectrum of the former compound yields peaks at 7.85–6.85, 5.48, 5.44, 4.43, and 1.40.

The IR (film, $\nu$max) spectrum reveals peaks at 1725, 1600, 1570, 1505, 1445, 1430, 1390, 1370, 1330, 1310, 1290, 1280, 1240, 1230, 1190, 1155, 1110, 1080, 1030, 1020, 905, 825, 760, 730, and 660 cm$^{-1}$.

The mass spectrum reveals an ion at m/e 270.1020.

The C:H:N ratio is 66.13:5.48:10.16.

The NMR (CDCl$_3$; TMS, $\delta$) spectrum of the latter compound reveals peaks at 7.82–6.92, 5.24, 4.45, and 1.42.

The IR (Nujol, $\nu$max) spectrum reveals peaks at 1725, 1700, 1570, 1510, 1320, 1300, 1230, 1220, 1200, 1150, 1100, 1080, 840, 760, and 750 cm$^{-1}$.

The mass spectrum reveals an ion at m/e 270.1012.

The C:H:N ratio is 66.79:5.53:10.21.

EXAMPLE 2

4-N-Imidazolylmethyl-benzofuran-2-carboxylic Acid, Sodium Salt (Formula I: Z$_3$ is imidazoly, X$_3$ is —CH$_2$— and is meta to the oxygen, R$_2$, R$_9$, and R$_{12}$ are hydrogen, D is a double bond, m is zero, and R$_7$ is —COONa)

A round-bottomed flask equipped with a magnetic stirring bar is charged with 135.2 mg (0.5 mmol) of the corresponding ester of Example 1, 0.55 ml of 1 N sodium hydroxide and 1.1 ml of methanol. The resulting mixture is stirred at room temperature for 18 hr.

The mixture is then lyophilized to give a white solid. This solid does not crystallize from acetone-water.

The NMR (CD$_3$OD+D$_2$O, TMS, $\delta$) spectrum reveals peaks at 8.02–7.00, 5.60 and 5.56.

EXAMPLE 3

5-N-Imidazolylmethyl-benzofuran-2-carboxylic Acid, Sodium Salt (Formula I: Z$_3$ is imidazolyl, X$_3$ is —CH$_2$— and is para to the oxygen, R$_2$, R$_9$ and R$_{12}$ are hydrogen, D is a double bond, m is zero, and R$_7$ is —COONa)

A round-bottomed flask equipped with a magnetic stirring bar is charged with 540.6 mg (2.0 mmol) of the corresponding ester of Example 1, 2.2 ml of 1 N sodium hydroxide and 4.4 ml of methanol. The resulting mixture is stirred at room temperature for 18 hr. The mixture is then lyophilized to give a white solid. Crystallization from acetone-water gives 503.5 mg (95%) of the sodium salt, with a melting point of greater than 270° C.

The NMR (CD$_3$OD+D$_2$O, TMS, $\delta$) spectrum reveals peaks at 7.85–7.02 and 5.34.

EXAMPLE 4

5-[(2-Methyl-1-imidazolyl)methyl]-benzofuran-2-carboxylic acid, ethyl ester and 4-[(2-methyl-1-imidazolyl)methyl]-benzofuran-2-carboxylic acid, ethyl ester (Formula I: Z$_3$ is 2-methyl-1-imidazolyl, X$_3$ is —CH$_2$— and is para or meta to the oxygen, R$_9$, R$_{12}$, and R$_2$ are hydrogen, m is zero, D is a double bond, and R$_7$ is —COOCH$_2$CH$_3$)

Refer to Chart A (conversion of XVI to XVII).

To a solution of 0.220 g of sodium hydride (60% oil dispersion) in dimethylformamide (10 ml) is added to a solution of 0.455 g of 2-methylimidazole in dimethylformamide (5 ml) over a five min period. Hydrogen gas evolution occurs. The stirred solution is heated to 90° C. for 1 hr under a nitrogen atmosphere then cooled to room temperature, after which 1.2 g of a 3:1 mixture of 5-(chloromethyl)-benzofuran-2-carboxylic acid, ethyl ester and the corresponding 4-chloromethyl isomer, dissolved in dimethylformamide (2 ml) was added. The resulting solution is stirred under a nitrogen atmosphere at room temperature for 1 hr before another 10 mg of sodium hydride (60% oil dispension) is added. The reaction mixture is stirred for an additional 1 hr more before again adding 20 mg of sodium hydride (60% oil dispersion). After 0.5 hr the reaction mixture is poured into 1:1 brine/water (100 ml) and the solution is extracted with methylene chloride (3×100 ml). The combined organic layers are washed with brine (100 ml), dried over magnesium sulfate and concentrated in vacuo to afford 1.68 g of residue. The residue is chromatographed on a 285 g of 40–60μ silica gel which is eluted with 5% methanol/methylene chloride and fractions of 25 ml are collected. Fractions 51–101 are combined and concentrated in vacuo to yield 1.00 g of residue. Fractions 159–260 are combined and concentrated in vacuo to yield approximately 0.2 g of material. Thin layer chromatography of the 1.0 g residue employing various solvent systems showed it to be two different materials. The 1.0 g product is therefore chromatographed on a 285 g high pressure liquid chromatography column which is eluted with 40% isopropanol/ethyl acetate and 25 ml fractions are collected. Fractions 41–45 are combined and concentrated in vacuo to yield 0.21 g of 5-substituted tilte compound. Fractions 48–86 are combined and concentrated in vacuo to yield 0.59 g of 7-substituted title compound. The combined yield of the two isomers is 51% of theory. A small amount of each isomer is recrystallized in diethyl ether. 5-Substituted title compound had a melting point range of 115°–117° C. and 4-substituted product has a melting point range of 134°–136° C.

The IR ($\nu$max (mull)) spectrum of the 5-substituted title compound reveals peaks at 1721, 1565, 1457, 1376, 1317, 1273, 1213, 1203, 1151, 764, and 741 cm$^{-1}$.

The NMR (CDCl$_3$; TMS, $\delta$) spectrum reveals peaks at 7.70–6.83, 5.17, 4.63–4.27, 2.35, and 1.57–1.27.

The mass spectrum reveals ions at m/e 284.1162, 285, 239, 204, 203, 175, 131, 102, 77, and 39.

TLC (silica gel GF) yields an R$_f$ of 0.32 (40% isopropanol/ethyl acetate).

The IR ($\nu$max (mull)) spectrum of the 4-substituted title product reveals peaks at 1717, 1698, 1466, 1427, 1392, 1376, 1371, 1329, 1303, 1290, 1234, 1187, 1113, 792, 772, 765, 749 cm$^{-1}$.

The NMR (CDCl$_3$; TMS, $\delta$) spectrum reveals peaks at 7.64–6.73, 5.36, 5.30, 4.58–4.25, 2.44, 2.34, and 1.51–1.33.

The mass spectrum reveals ions at m/e 284.1168, 285, 211, 204, 203, 176, 175, 131, 102, and 77.

TLC (silica gel GF) yields an R$_f$ of 0.41 (40% isopropanol/ethyl acetate).

EXAMPLE 5

5-[(2-Methyl-1-imidazolyl)methyl]-benzofuran-2-carboxylic acid, sodium salt (Formula I: Z$_3$ is 2-methyl-1-imidazolyl, X$_3$ is para to the oxygen, R$_9$ and R$_{12}$ are hydrogen, m is zero, D is a double bond, and R$_7$ is —COONa)

To a solution of 0.4457 g of 5-[(2-methyl-1-imidazolyl)methyl]-benzofuran-2-carboxylic acid, ethyl ester in 8 ml of tetrahydrofuran is added 14.89 ml of 0.10 M aqueous sodium hydroxide. The reaction mixture is stirred under a nitrogen atmosphere at room temperature for 26 hr before concentrating in vacuo to dryness. The resulting residue is triturated with acetonitrile (5 ml) for 2 hr. The mixture is filtered and the crystals washed with acetonitrile (2 ml), then dried in vacuo for 33 hr to yield 0.395 g of product (95% of theory) with a melting point greater than 300° C.

The IR ($\nu$max, (mull)) spectrum reveals peaks at 1603, 1566, 1533, 1429, 1407, 1391, 1378, 1357, 1284, 1138, 943, 935, 805, 793, 766, and 762 cm$^{-1}$.

EXAMPLE 6

4-[(2-Methyl-1-imidazolyl)methyl]-benzofuran-2-carboxylic acid, sodium salt (Formula I: Z$_3$ is 2-methyl-1-imidazolyl, X$_3$ is meta to the oxygen, R$_9$ and R$_{12}$ are hydrogen, m is zero, D is a double bond, and R$_7$ is —COONa)

To a solution of 0.1138 g of 4-[(2-methyl-1-imidazolyl)methyl]-benzofuran-2-carboxylic acid, ethyl ester in 8 ml of tetrahydrofuran is added 3.80 ml of 0.10 M aqueous sodium hydroxide. The reaction stirred at room temperature under a nitrogen atmosphere for 26 hr. The solution is concentrated in vacuo to dryness and the residue is triturated with acetonitrile (3 ml) for 2 hr. The solution is filtered and the crystals washed with acetonitrile (2 ml), and hen dried in vacuo for 33 hr to yield 66 mg of pure product (79% of theory) with melting point 180°–200° C.

The IR ($\nu$max, (mull)) spectrum reveals peaks at 3367, 1615, 1568, 1530, 1501, 1495, 1462, 1459, 1426, 1387, 1346, 1285, 1186, 1155, 1132, 1077, 944, 811, 784, 766, 745, and 723 cm$^{-1}$.

EXAMPLE 7

4-[(4-Methyl-1-imidazolyl)methyl]-benzofuran-2-carboxylic acid, ethyl ester and 4-[(4-methyl-1-imidazolyl)methyl]-benzofuran-2-carboxylic acid, ethyl ester (Formula C-I: Z$_3$ is 4-methyl-1-imidazolyl, X$_3$ is —CH$_2$— and is para to the oxygen, R$_9$, R$_{12}$, and R$_2$ are hydrogen, D is a double bond, m is zero, and R$_7$ is —COOCH$_2$CH$_3$)

Refer to Chart A (conversion of XV to XVII).

A 50 ml round-bottomed, 2-necked flask fitted with a condenser and magnetic stirrer, is flame-dried, then cooled in an atmosphere of nitrogen. The flask is then charged with 220 mg (5.5 mmol) of sodium hydride (60% dispension), from which the oil is washed with two 5 ml portions of hexane. (Hexane is removed with vacuum via a micro gas dispersion tube.) Dimethylformamide (10 ml) is added, and the stirred suspension is treated over 5 min with a solution of 455 mg (5.5 mmol) of 4-methylimidazole in 2 ml of dimethylformamide (hydrogen evolution). The mixture is stirred at 90° for 1 hr (probably more vigorous than necessary) and became a clear light yellow solution. This solution is recooled to ambient temperature and treated with a solution of 1.2 g (5 mmol) of a 3:1 mixture of 5-(chloromethyl)-benzofuran-2-carboxylic acid ethyl ester and the corresponding 4-chloromethyl isomer in 2 ml of dimethylformamide over 5 min. Although sodium chloride began to precipitate almost immediately, TLC analysis of an aliquot after 1 hr of stirring at 25° showed that about 10–15% of starting chloro-ester 1 remained. More sodium hydride (20 mg) is added, and the mixture is stirred for an additional 45 min.

The reaction mixture is poured into 1:1 brine/water and extracted thoroughly with methylene chloride. The extracts are washed with water several times, then with brine, dried over sodium sulfate and concentrated in vacuo. Residual dimethylformamide is removed in a stream of nitrogen (16 hr).

The crude product (1.5 g) is chromatographed on a column containing 150 g of silica gel. The column is packed and eluted (15 ml fractions) with 60% acetone/methylene chloride.

Fractions 90–108 are combined based on their TLC homogeneity and afford 233 mg of 4-substituted benzofuran derivative (title compound), a light yellow oil.

The IR ($\nu$max (neat)) spectrum reveals peaks at 3100, 1710, 1595, 1560, 1490, 1440, 1365, 1300, 1290, 1240, 1180, 1100, 1015, 945, 760, 660, and 620 cm$^{-1}$.

The NMR (CDCl$_3$; TMS, $\delta$) spectrum reveals peaks at 7.6–6.6, 5.41, 5.30, 4.58–4.31, 2.21 and 1.42.

The mass spectrum reveals ions at m/e 284.1160, 239, 203, 175, 131, 102, and 77.

TLC (silica gel GF) yields an R$_f$ of 0.26 (70% acetone/methylene chloride).

Continued elution of the above chromatogram with 60% acetone/methylene chloride affords (fractions 120–161) 618 mg of 5-substituted title compound. This material, homogeneous by TLC, cyrstallizes spontaneously and upon recrystallization from ether/hexane yields 320 mg of 5-substituted title compound with melting point 68°–71° C.

The IR ($\nu$max (mull)) spectrum reveals peaks at 2930, 2856, 1725, 1466, 1375, 1332, 1316, 1298, 1234, 1200, 1143, 1010, 835, 766, 760, 742 cm$^{-1}$.

The NMR (CDCl$_3$; TMS, $\delta$) spectrum reveals peaks at 7.63–6.62, 5.15, 4.58–4.31, 2.23, 2.10, and 1.42.

The mass spectrum reveals ions at m/e 284.1154, 239, 203, 175, 157, 131, 119, 102, 77, 63, and 51.

TLC (silica gel GF) yields an R$_f$ of 0.19 (70% acetone/methylene chloride).

EXAMPLE 8

5-[(4-Methyl-1-imidazolyl)methyl]-benzofuran-2-carboxylic acid, sodium salt (Formula I: Z$_3$ is 4-methyl-1-imidazolyl, X$_3$ is —CH$_2$— and is para to the oxygen, R$_9$ and R$_{12}$ are hydrogen, D is a double bond, m is zero, and R$_7$ is —COONa)

A solution of 150 mg of the 5-substituted isomer from Example 10 in 5 ml of methanol is treated with 5.0 ml of 0.1 M aqueous sodium hydroxide and the resulting clear solution is stirred for 64 hr at 25° in an atmosphere of nitrogen. The methanol and water are removed on the rotary evaporator, and the residue is triturated with acetonitrile (approximately 5 ml). Filtration, washing of the solids with about 1 ml of fresh acetonitrile and drying (25°, 0.1 mm, 16 hr) affords 123 mg (85% of theory) of pure sodium salt title product melting point of 290°–294° C.

The IR ($\nu$max (mull)) spectrum reveals peaks at 3350, 1614, 1570, 1502, 1450, 1378, 942, 789 and 763 cm$^{-1}$.

EXAMPLE 9

4-[(4-Methyl-1-imidazolyl)methyl]-benzofuran-2-carboxylic acid, sodium salt (Formula C-I: Z$_3$ is 4-methyl-1-imidazolyl, X$_3$ is meta to the oxygen, R$_9$ and R$_{12}$ are hydrogen, D is a double bond, m is zero, and R$_7$ is —COONa)

Using a procedure and amounts identical to those in the preceding experiment, 150 mg of 4-substituted ethyl ester is converted to the sodium salt. The crude salt is triturated with 5 ml of acetonitrile, filtered, washed with additional acetonitrile, and dried (16 hr, 25°, 0.1 mm), thereby affording 84 mg of pure title compound, melting point 237°–240° C.

The IR ($\nu$max (mull)) spectrum reveals peaks at 3371, 1613, 1567, 1504, 1455, 1380, 1345, 1185, 1157, 1107, 944, 812, 785 and 760 cm$^{-1}$.

TABLE I

FORMULA

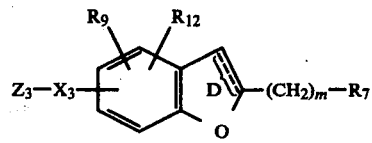

I

CHART A

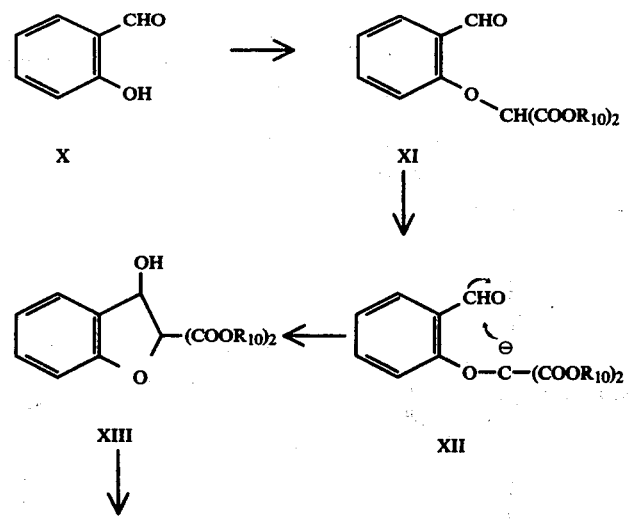

CHART A
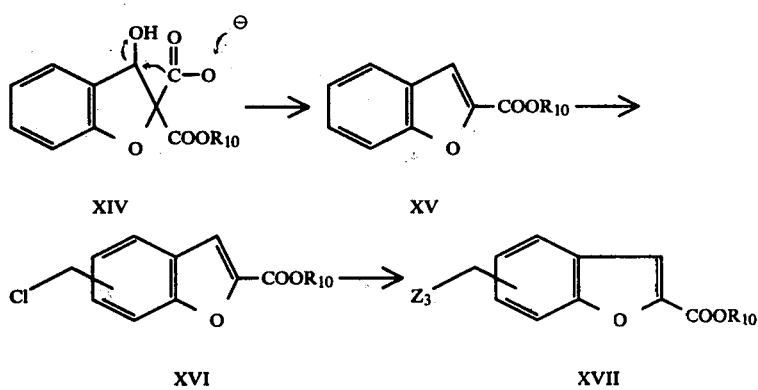
CHART B
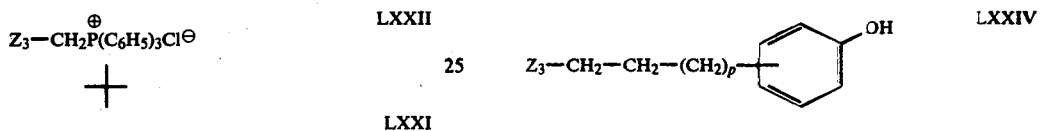
LXXII
-continued
CHART B
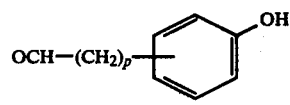 LXXIV
LXXI
CHART C
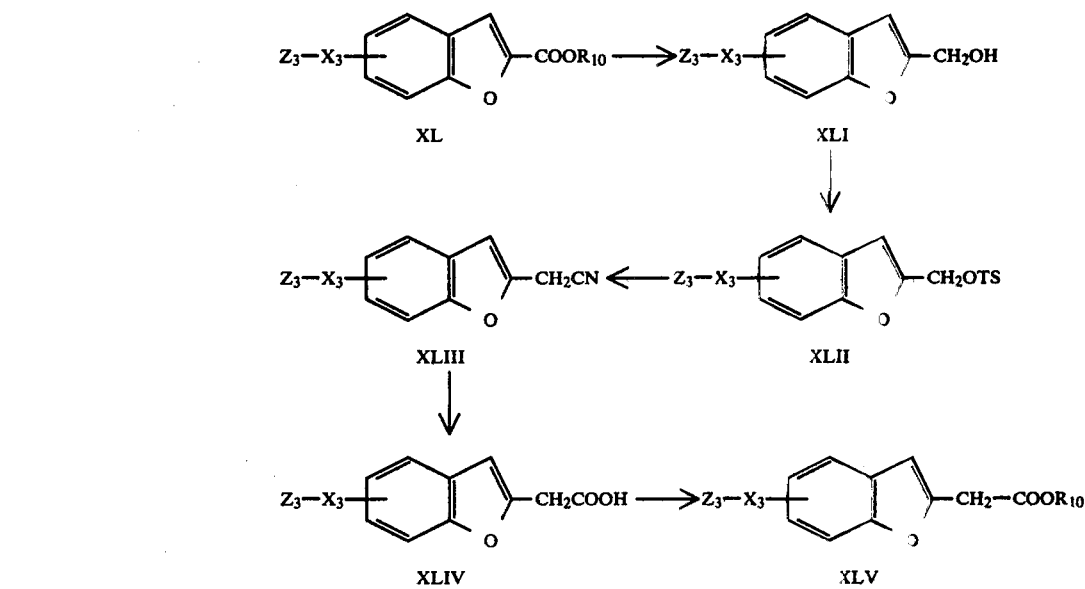
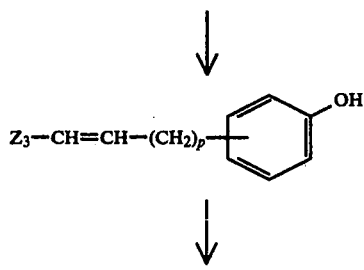
LXXIII
CHART D -continued
CHART D
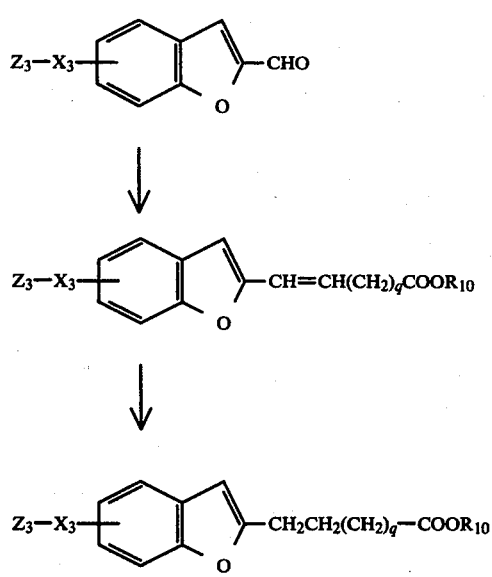
CHART E
CHART F
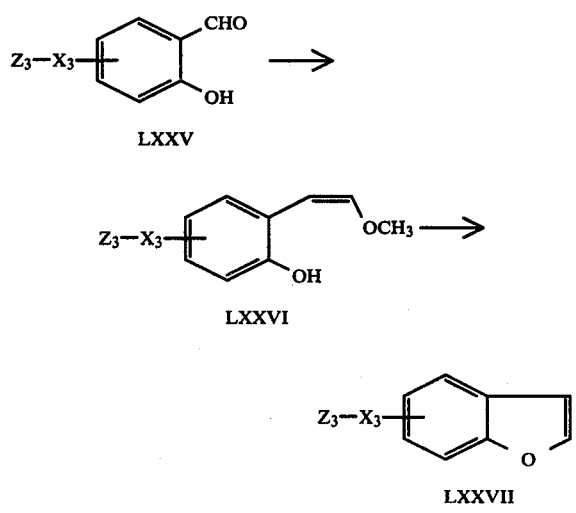
CHART G
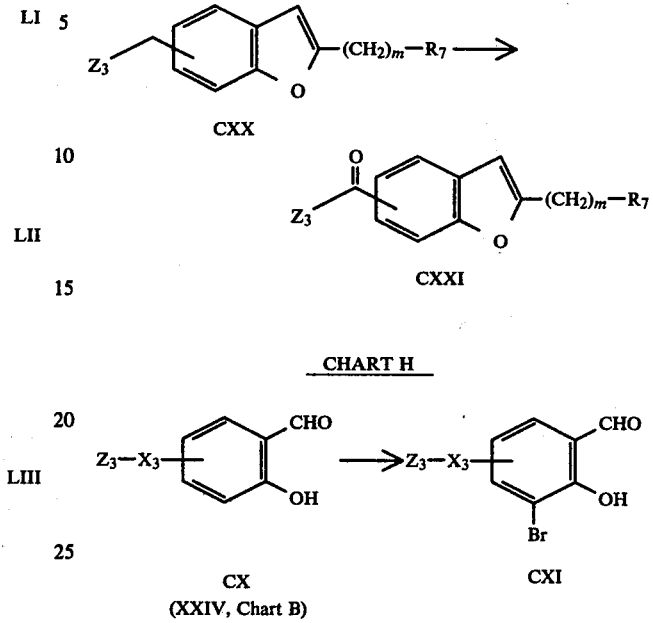
CHART H
CHART I
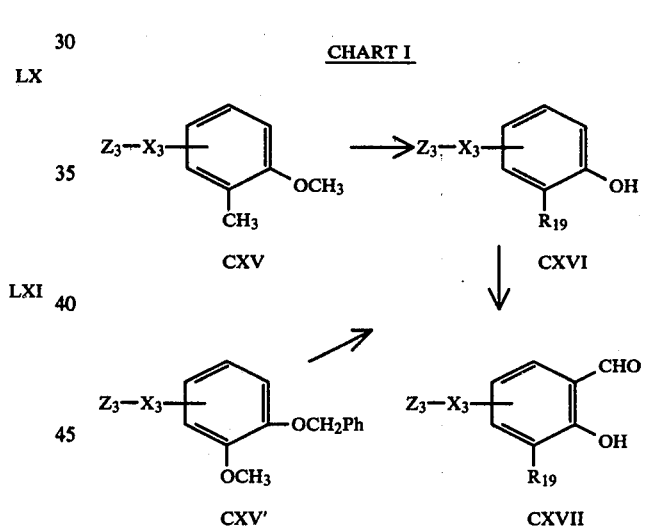
We claim:
1. A compound of the formula I
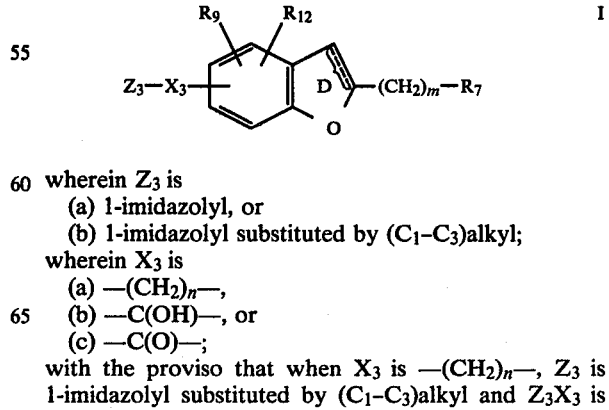
wherein $Z_3$ is
  (a) 1-imidazolyl, or
  (b) 1-imidazolyl substituted by $(C_1-C_3)$alkyl;
wherein $X_3$ is
  (a) $-(CH_2)_n-$,
  (b) $-C(OH)-$, or
  (c) $-C(O)-$;
with the proviso that when $X_3$ is $-(CH_2)_n-$, $Z_3$ is 1-imidazolyl substituted by $(C_1-C_3)$alkyl and $Z_3X_3$ is attached to the 4-position of the benzofuran, and n is not zero, wherein $R_1$ is hydrogen, a pharmacologically acceptable cation, $(C_1-C_{12})$ alkyl, $(C_3-C_{10})$ cycloalkyl, $(C_7-C_{12})$ aralkyl, phenyl, phenyl mono-, di-, or trisubstituted by chloro, $(C_1-C_3)$ or alkyl, or phenyl para-substituted by
 (a) —NHCO—$R_{25}$,
 (b) —O—CO—$R_{26}$,
 (c) —CO—$R_{24}$,
 (d) —O—CO—(p-Ph)—$R_{27}$, or
 (e) —CH=N—NH—CO—NH$_2$, wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy; and $R_{27}$ is hydrogen or acetamido, and wherein —(p-Ph) is 1,4-phenylene;

wherein $R_4$ is
 (a) hydrogen,
 (b) $(C_1-C_4)$alkyl, or
 (c) phenyl;

wherein $R_7$ is
 (a) hydrogen,
 (b) —CH$_2$OH,
 (c) —COOR$_1$,
 (d) —CH$_2$N(R$_4$)$_2$,
 (e) —CN
 (f) —CON(R$_4$)$_2$, or
 (g) —C(O)—R$_4$;

wherein $R_9$ and $R_{12}$ are the same or different and are
 (a) hydrogen,
 (b) $(C_1-C_4)$alkyl
 (c) fluoro,
 (d) chloro,
 (e) bromo,
 (f) —OCH$_3$, or,
 (g) when taken together and attached to contiguous carbon atoms, —O—CH$_2$—O—;

wherein D represents a single or a double bond; and wherein m and n are the same or different and are the integers 0 to 4, inclusive; or a pharmacologically acceptable acid addition salt thereof; or when D represents a single bond, an enantiomer or a racemic mixture of enantiomers thereof.

2. A compound of claim 1, wherein D denotes a double bond, $X_3$ is —(CH$_2$)$_n$—, n is one, m is zero, $R_9$ and $R_{12}$ are hydrogen, and $R_7$ is —COOR$_1$.

3. A compound of claim 2, selected from the group consisting of:
4-[(2-methyl-1-imidazolyl)methyl]-benzofuran-2-carboxylic acid, ethyl ester,
4-[(2-methyl-1-imidazolyl)methyl]-benzofuran-2-carboxylic acid, sodium salt,
4-[(4-methyl-1-imidazolyl)methyl]-benzofuran-2-carboxylic acid, ethyl ester, and
4-[(4-methyl-1-imidazolyl)methyl]-benzofuran-2-carboxylic acid, sodium salt.

4. 4-[(2-Methyl-1-imidazolyl)methyl]-benzofuran-2-carboxylic acid, ethyl ester, a compound of claim 3.

5. 4-[(2-Methyl-1-imidazolyl)methyl]-benzofuran-2-carboxylic acid, sodium salt, a compound of claim 3.

6. 4-[(4-Methyl-1-imidazolyl)methyl]-benzofuran-2-carboxylic acid, ethyl ester, a compound of claim 3.

7. 4-[(4-Methyl-1-imidazolyl)methyl]-benzofuran-2-carboxylic acid, sodium salt, a compound of claim 3.

* * * * *

UNITED STATES PATENT OFFICE
CERTIFICATE OF CORRECTION

Patent No. 4,452,986                   Dated   5 June 1984

Inventor(s)   Roy A. Johnson

It is certified that error appears in the above-identified patent and that said Letters Patent are hereby corrected as shown below:

Column 11, line 58, "7.64-6.73," should read -- 7.65-6.73, --.
Column 12, line 32, "and hen dried" should read -- and then dried --.
Column 12, line 41, "4-[(4-" should read -- 5-[(4- --.
Column 18, line 67, "-$(CH_2)_n$-, $Z_3$ is" should read -- -$(CH_2)_n$- and n is not zero, $Z_3$ is --.
Column 19, lines 1-2, "benzofuran, and n is not zero, wherein " should read -- benzofuran, wherein --.

Signed and Sealed this

Twenty-second Day of October 1985

[SEAL]

Attest:

Attesting Officer

DONALD J. QUIGG

Commissioner of Patents and Trademarks—Designate